(12) United States Patent
Mustapha (10) Patent No.: US 11,338,081 B2
(45) Date of Patent: May 24, 2022

(54) FLUID MIXING DEVICE

(76) Inventor: Jihad Mustapha, Ada, MI (US)

( * ) Notice: Subject to any disclaimer, the term of this patent is extended or adjusted under 35 U.S.C. 154(b) by 182 days.

(21) Appl. No.: 13/425,898

(22) Filed: Mar. 21, 2012

(65) Prior Publication Data

US 2012/0247614 A1     Oct. 4, 2012

Related U.S. Application Data

(60) Provisional application No. 61/471,300, filed on Apr. 4, 2011.

(51) Int. Cl.
| | | |
|---|---|---|
| *A61M 5/00* | (2006.01) | |
| *A61M 39/22* | (2006.01) | |
| *A61M 5/14* | (2006.01) | |
| *B01F 33/501* | (2022.01) | |
| *B01F 35/71* | (2022.01) | |
| *B01F 35/75* | (2022.01) | |

(52) U.S. Cl.
CPC .......... *A61M 5/007* (2013.01); *A61M 5/1408* (2013.01); *A61M 39/223* (2013.01); *B01F 33/50111* (2022.01); *B01F 35/718* (2022.01); *B01F 35/7543* (2022.01)

(58) Field of Classification Search
CPC ............ B01F 33/50111; B01F 35/7543; B01F 35/718; A61M 5/007; A61M 5/1408; A61M 39/223
USPC ... 141/27, 99, 103, 105, 107, 234, 302, 329, 141/330; 604/183, 187, 236, 247, 258, 604/404–416
See application file for complete search history.

(56) References Cited

U.S. PATENT DOCUMENTS

| | | | | |
|---|---|---|---|---|
| 1,769,941 | A | * | 7/1930 | Miller ............................ 141/18 |
| 2,525,419 | A | * | 10/1950 | McLlinger et al. .......... 604/118 |
| 2,584,397 | A | * | 2/1952 | Pitman ........................... 141/59 |
| 3,273,402 | A | * | 9/1966 | Farr ........................... 73/864.12 |
| 3,401,698 | A | * | 9/1968 | Rosecrans .................. 604/98.01 |
| 3,559,703 | A | * | 2/1971 | Maul et al. ................... 141/329 |
| 3,886,937 | A | * | 6/1975 | Bobo et al. ..................... 604/81 |
| 3,982,534 | A | * | 9/1976 | Buckman ........................ 604/81 |
| 4,041,994 | A | * | 8/1977 | Horwitz et al. .................. 141/1 |
| 4,067,366 | A | * | 1/1978 | Conway et al. ................ 141/59 |
| 4,191,183 | A | * | 3/1980 | Mendelson ..................... 604/80 |
| 4,296,785 | A | * | 10/1981 | Vitello et al. ................. 141/105 |
| 4,344,469 | A | * | 8/1982 | Brown ............................ 141/90 |

(Continued)

*Primary Examiner* — Timothy P. Kelly
(74) *Attorney, Agent, or Firm* — Michele V. Frank; Venable LLP (57) ABSTRACT

A fluid mixing device includes inlet ports in fluid communication with respective source containers, an inlet check valve, a mixing container in fluid communication with the inlet check valve, a discharge port in fluid communication with a target container, and a discharge check valve in fluid communication with the mixing container and the discharge port. Responsive to a negative pressure at the mixing container, fluid is drawn from the respective source containers through the inlet ports and through the inlet check valve and into the mixing container, while the discharge check valve precludes drawing of fluid from the target container. Responsive to a positive pressure at the mixing container, fluid is expelled from the mixing container through the discharge check valve and into the target container, while the inlet check valve precludes discharge of fluid from the mixing container to the inlet ports and the source containers.

20 Claims, 7 Drawing Sheets

(56) References Cited

U.S. PATENT DOCUMENTS

| | | | | |
|---|---|---|---|---|
| 4,372,100 | A * | 2/1983 | Miller et al. | 53/428 |
| 4,447,230 | A * | 5/1984 | Gula et al. | 604/122 |
| 4,625,494 | A * | 12/1986 | Iwatschenko et al. | 53/432 |
| 4,635,825 | A * | 1/1987 | Tulasne | 222/129.1 |
| 4,737,037 | A * | 4/1988 | Mojonnier | 366/152.1 |
| 4,786,286 | A * | 11/1988 | Cerny et al. | 604/406 |
| 4,883,459 | A * | 11/1989 | Calderon | 604/28 |
| 5,037,390 | A * | 8/1991 | Raines et al. | 604/83 |
| 5,254,313 | A * | 10/1993 | Kuroda et al. | 422/514 |
| 5,289,858 | A * | 3/1994 | Grabenkort | 141/97 |
| 5,329,976 | A * | 7/1994 | Haber et al. | 141/25 |
| 5,522,804 | A * | 6/1996 | Lynn | 604/191 |
| 6,131,601 | A * | 10/2000 | Schiller et al. | 137/101.27 |
| 6,186,193 | B1 * | 2/2001 | Phallen et al. | 141/83 |
| 6,336,572 | B1 * | 1/2002 | Fujikawa et al. | 222/380 |
| 7,316,662 | B2 * | 1/2008 | Delnevo et al. | 604/6.16 |
| 7,322,956 | B2 * | 1/2008 | Fehr et al. | 604/82 |
| 8,596,307 | B2 * | 12/2013 | Krulitsch et al. | 141/9 |
| 2001/0009994 | A1 * | 7/2001 | Small et al. | 604/513 |
| 2002/0104584 | A1 * | 8/2002 | Spero et al. | 141/329 |
| 2007/0088252 | A1 * | 4/2007 | Pestotnik et al. | 604/82 |
| 2009/0145509 | A1 * | 6/2009 | Baker et al. | 141/2 |
| 2009/0182263 | A1 * | 7/2009 | Burbank et al. | 604/28 |
| 2010/0009008 | A1 * | 1/2010 | Watson et al. | 424/600 |
| 2010/0030074 | A1 * | 2/2010 | Imai et al. | 600/432 |
| 2010/0034705 | A1 * | 2/2010 | Mundt et al. | 422/100 |
| 2010/0298699 | A1 * | 11/2010 | Reilly et al. | 600/432 |
| 2010/0305507 | A1 * | 12/2010 | Duncan | 604/121 |
| 2010/0331773 | A1 * | 12/2010 | Frederiksen et al. | 604/84 |
| 2011/0009837 | A1 * | 1/2011 | Schreiner | 604/317 |
| 2012/0029464 | A1 * | 2/2012 | Kragelund et al. | 604/414 |
| 2012/0053457 | A1 * | 3/2012 | Fago | 600/432 |
| 2012/0172829 | A1 * | 7/2012 | Hasegawa et al. | 604/405 |

\* cited by examiner

FLUID MIXING DEVICE

CROSS REFERENCE TO RELATED APPLICATION

The present application claims the filing benefit of U.S. provisional application Ser. No. 61/471,300, filed Apr. 4, 2011, which is hereby incorporated herein by reference in its entirety.

FIELD OF THE INVENTION

The present invention relates to devices for mixing fluids for a patient and, more particularly, to a device for mixing contrast with a saline solution or the like.

BACKGROUND OF THE INVENTION

It is known to mix solutions to a desired percentage or content ratio, such as for mixing fluids with saline or the like for use with patients. It is important to keep the base solutions clean or non-contaminated during the mixing process, so that only the correct or selected amounts of the base solutions are mixed together in the desired ratios for use with a particular patient.

SUMMARY OF THE INVENTION

The present invention provides a fluid mixing device that mixes two (or more) fluids or solutions together when drawing the solutions from their respective source containers, and discharges the mixture or mixed solution into a target container or vessel, without discharging the mixed solution back into the respective source containers.

According to an aspect of the present invention, a fluid mixing device for mixing fluids from at least two source containers and for discharging a mixed solution to a target container includes first and second inlet ports in fluid communication with respective source containers and at least one one-way flow inlet check valve in fluid communication with the first and second inlet ports. A mixing container is in fluid communication with the at least one one-way flow inlet check valve, and a discharge port in fluid communication with a target container, with a one-way flow discharge check valve in fluid communication with the mixing container and the discharge port. Responsive to a negative pressure at the mixing container, fluid is drawn from the respective source containers through the first and second inlet ports and through the at least one one-way flow inlet check valve and into the mixing container, while the one-way flow discharge check valve precludes drawing of fluid from the target container. Responsive to a positive pressure at the mixing container, fluid is expelled from the mixing container through the one-way flow discharge check valve and into the target container, while the at least one one-way flow inlet check valve precludes discharge of fluid from the mixing container to the inlet ports and the source containers.

The ports and check valves may be disposed at and in a housing, with the ports being at an outer portion of the housing to allow for connection and disconnection of the mixing device to the source tubes and source containers and the mixing container and the target container. The housing may include one or more user inputs to allow a user to control the size of the passageway through which the fluid flows into the mixing device from the source containers, so as to facilitate control of the percentage of fluids in the final mixture.

These and other objects, advantages, purposes and features of the present invention will be more fully understood and appreciated by reference to the below description of the preferred embodiments and the drawings.

DESCRIPTION OF THE PREFERRED EMBODIMENTS

Referring now to the drawings and the illustrative embodiments depicted therein, a contrast (or other dye or solution) mixing device 10 functions to draw separate, non-mixed fluids or solutions out of respective source containers, mix the fluids or solutions together at the desired mix ratio, and discharge the mixed solution to another container or vessel or to a patient, without discharging the mixed solution back into either of the source containers (FIGS. 1-7). The contrast mixing device 10 includes two inlet ports 12a, 12b (but could include three or more inlet ports) into and through which the source fluids are drawn, such as via providing a negative pressure at a mixing port 22, as discussed below. The mixed solution is discharged through a discharge port 30 to another container or to the patient, while the contrast mixing device 10 limits or substantially precludes any discharge of the mixed solution through inlet ports 12a, 12b and back into the source containers, so that the fluids in the source containers remain uncontaminated during and after the mixing process, as also discussed below.

Contrast induced nephropathy is one of the more common complications post coronary and peripheral angiography. Also, calculated contrast utilization often limits the operator or physician to partial angiography and/or interventions in otherwise needed situations. The contrast mixing device of the present invention provides a device that controls the flow of fluids entering and exiting the device to provide for mixing of the fluids (such as the contrast fluid and saline or the like) to the desired or appropriate ratio or concentration and to provide for the discharge of the mixed fluid in a controlled manner.

Figure 1:
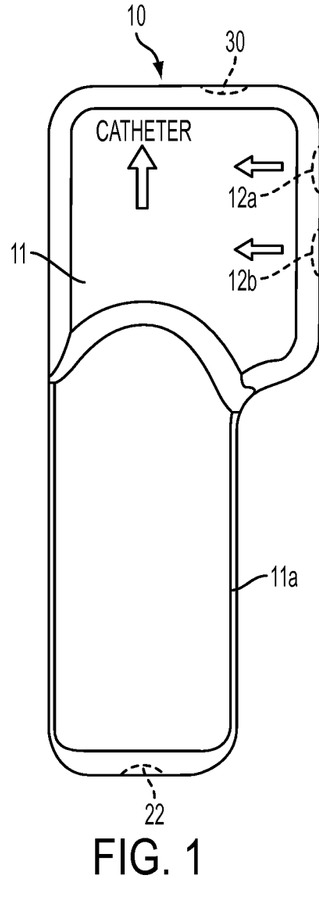
FIG. 1 is a side elevation of a fluid mixing device in accordance with the present invention.
Figure 2:
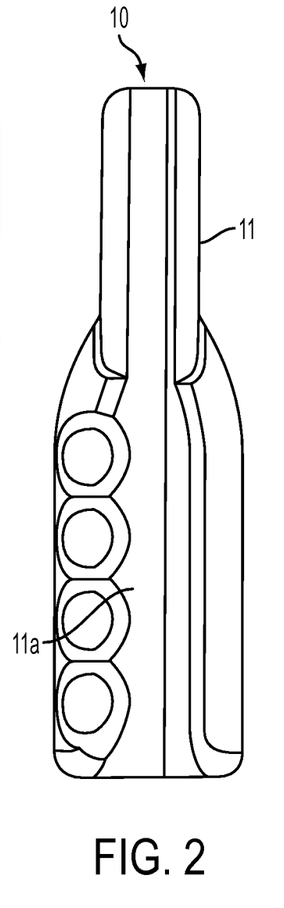
FIG. 2 is an end elevation of the fluid mixing device of FIG. 1.
Figure 3:
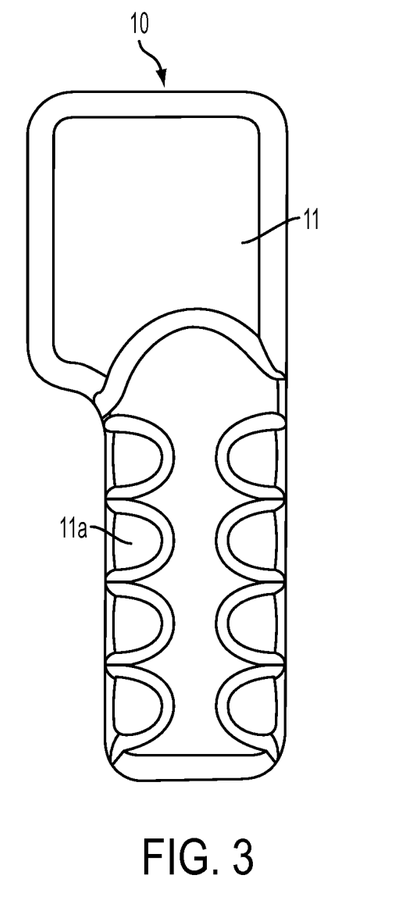
FIG. 3 is an opposite side elevation of the fluid mixing device of FIG. 1.
Figure 4:
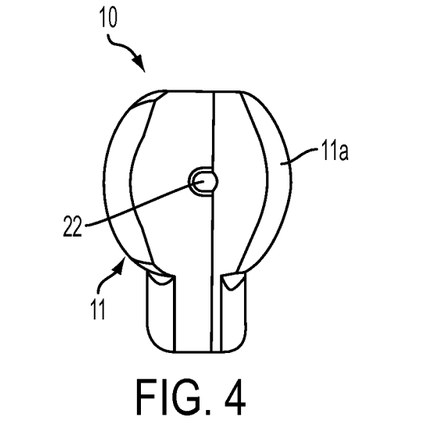
FIG. 4 is a bottom plan view of the fluid mixing device of FIG. 1.
Figure 5:
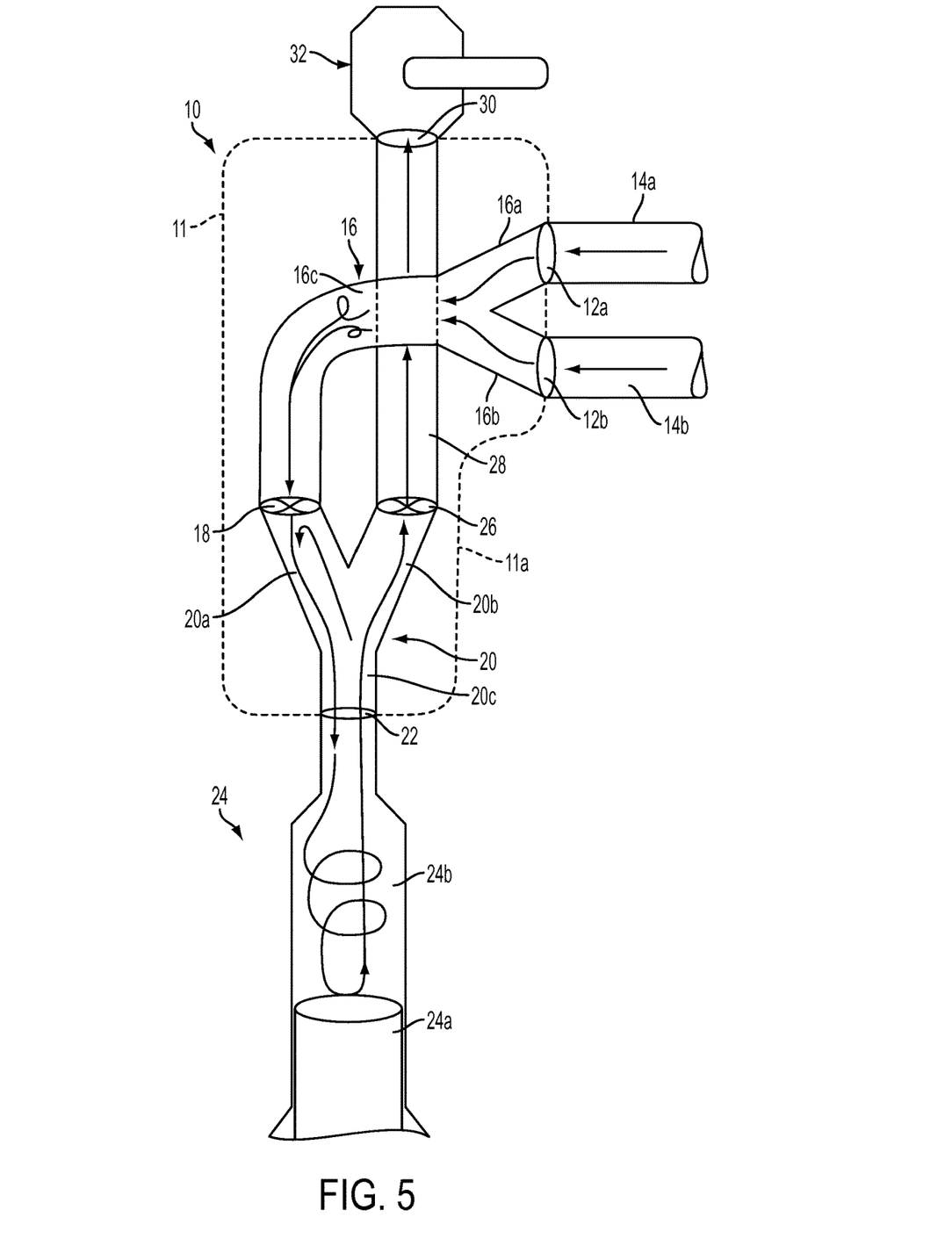
FIG. 5 is a schematic of the tubes and valves of the fluid mixing device of the present invention.
Figure 6:
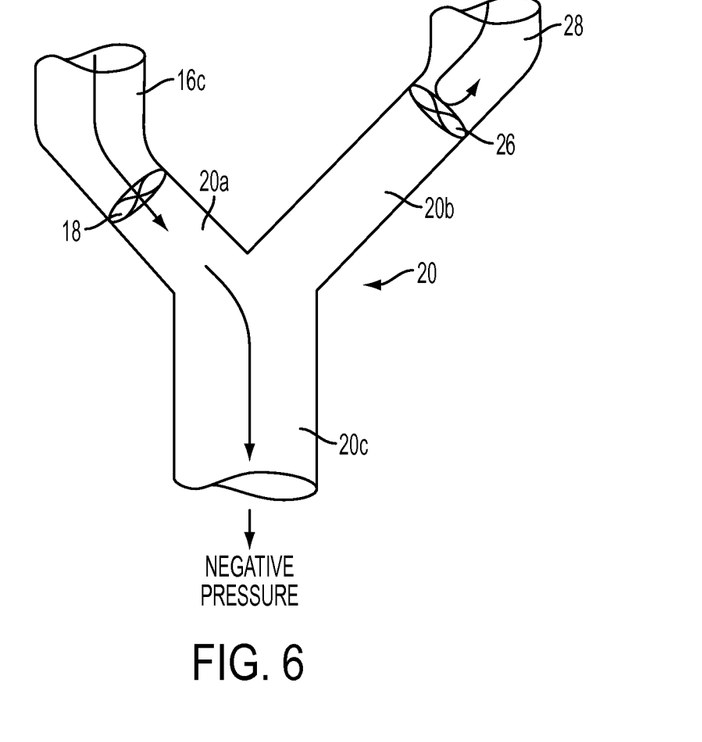
FIG. 6 is an enlarged plan view of a portion of the tubes and valves of the fluid mixing device of FIG. 5, showing the flow of fluids during the mixing stage of use of the fluid mixing device.
Figure 7:
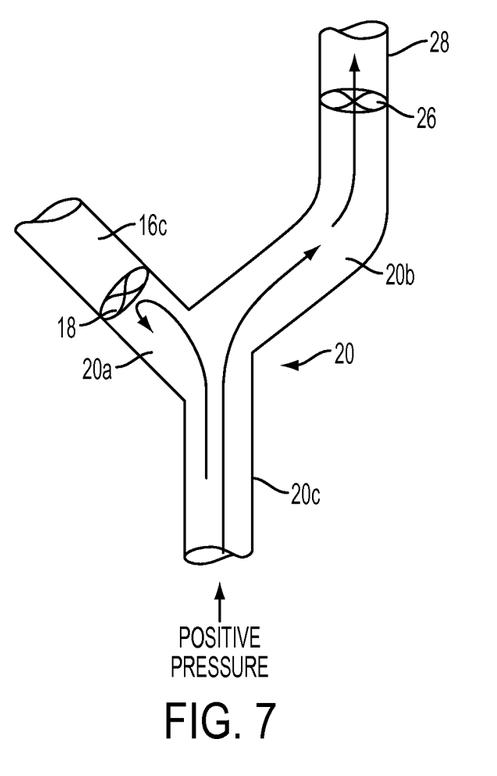
FIG. 7 is another enlarged view of FIG. 6 showing the flow of fluids during the injection stage of use of the fluid mixing device of the present invention.

In the illustrated embodiment, the contrast mixing device 10 comprises a hand-held device having ports and tubes or pipes and valves housed or contained within a housing or casing 11 (which may have a handle portion or gripping portion 11a or the like to ease the user's handling of the device during use). The hand-held mixing device functions to draw fluid from two sources or source containers (but could draw from more source containers depending on the particular application of the device) into the device, mix the fluids, either in the device or in a syringe or negative pressure device attached to a portion of the contrast mixing device, and discharge the mixed fluid from the device to the patient or receptacle for the mixed fluid, all in a controlled manner that allows for control of the mixing proportions and avoids flow of the fluids in an undesired direction. As shown in FIG. 5, the contrast mixing device 10 includes inlet ports 12a, 12b for connecting to inlet tubes 14a, 14b of two separate fluid supply sources (such as a supply of contrast and a supply of saline solution or the like).

The contrast mixing device 10 includes a first Y-shaped tube 16 disposed therein, with the two different branches 16a, 16b connecting to or terminating at the inlet ports 12a, 12b, and with the opposite end of the first Y-shaped tube 16 having a single tube or branch 16c, which terminates at or includes or is in fluid connection with a one way flow or check valve 18 (with the check valve, in the illustrated embodiment, being disposed anywhere downstream of the junction of the branches 16a, 16b). Check valve 18 allows fluid flow from inlet ports 12a, 12b through the first Y-shaped tube 16 and into a tube or branch 20a of another generally Y-shaped tube 20 (hereinafter "second Y-shaped tube 20"), while limiting fluid flow in the opposite direction. Although shown as having a single check valve 18 downstream from the first Y-shaped tube 16, it is envisioned that each branch 16a, 16b (in fluid communication with the respective inlet ports 12a, 12b) may have a respective check valve disposed thereat, such that fluid is drawn through the two check valves (such as at the desired ratio, as discussed below) and into the first Y-shaped tube 16 and further into and through the second Y-shaped tube 20 to mix the solution in the mixing container, while remaining within the spirit and scope of the present invention.

The second Y-shaped tube 20 includes two branches 20a, 20b and a common stem or tube 20c that extends from the junction of the two branches 20a, 20b to the mixing port 22 of contrast mixing device 10 for connection to a syringe or other fluid collecting and mixing device 24. The branch 20b of the second Y-shaped tube 20 includes or terminates at or is in fluid connection with another one way flow valve or check valve 26, which allows for fluid to flow from branch 20b into a discharge tube 28 that extends to a discharge port 30 of hand held contrast mixing device 10. Discharge port 30 may connect to a tube or pipe or hose that connects to a fluid collecting container 32 or the like or to the patient that is to receive the mixed contrast-saline solution, as discussed below.

Thus, and as best shown in FIG. 5, when a negative pressure is applied at syringe 24 (such as via an operator drawing back on the plunger 24a of the syringe 24 to draw fluid into the cylinder or cavity or receptacle 24b of the syringe), fluid from inlet tubes 14a, 14b is drawn into the inlet ports 12a, 12b and into branches 16a, 16b of the first Y-shaped tube 16 and through check valve 18 and into branch 20a of the second Y-shaped tube 20 and into common tube 20c of the second Y-shaped tube 20 and through the mixing port 22 and into the mixing container or portion or receptacle 24b of the syringe or negative pressure device 24. The fluid is mixed as it is drawn through the first Y-shaped tube 16 and into the receptacle 24b to substantially mix the two liquids or solutions together to provide a substantially uniform mixture or composition (as can be seen in FIG. 5, the drawing in of fluids generates turbulence in the tube 16c to mix the fluids and further turbulence is generated as the mixed fluids are drawn into the syringe or mixing container). During the drawing in of fluid through the inlet ports 12a, 12b of the contrast mixing device, check valve 26 (which allows fluid flow from the mixing port 22 towards the discharge port 30, but limits or substantially precludes fluid flow in the opposite direction) at discharge tube 28 limits or substantially precludes any drawing of fluid from the receptacle 32 into the discharge tube 28 and branch 20b of the second Y-shaped tube 20, such that only the fluid from the desired sources (the source containers connected to inlet ports 12a, 12b of mixing device 10 via inlet tubes 14a, 14b) is drawn into the mixing device and mixed together.

After the solutions are mixed and a sufficient or desired or selected or prescribed quantity of mixed solution is at the container 24b, a positive pressure may be applied at container 24b (such as via a user pushing on the plunger 24a of syringe 24) to impart fluid flow from the container or vessel 24b back into the device 10 through the mixing port 22 and towards and into the target container or receptacle or vessel 32. When the positive pressure is applied at the syringe 24 or receptacle 24b, the mixed fluid flows through the mixing port 22 and into the common tube 20c of the second Y-shaped tube 20 and into branch 20b and through check valve 26 (which allows fluid flow in the discharge direction) and through discharge tube 28 and out of discharge port 30 and into the target receptacle 32. During the discharge of the mixed fluid, check valve 18 (which allows fluid flow from the inlet ports 12a, 12b towards the mixing port 22, but limits or substantially precludes fluid flow in the opposite direction) at branch 20a of the second Y-shaped tube 20 limits or substantially precludes any of the mixed fluid from flowing back into the first Y-shaped tube 16 and into the source containers at inlet tubes 14a, 14b, such that all of the mixed fluid flows into the targeted receptacle 32.

Thus, the inlet tube 14a at inlet port 12a may deliver the solution that is to be mixed with the solution delivered from the other inlet tube 14b at inlet port 12b. The solution in inlet tube 14a may comprise any suitable solution that can be used in human subjects, such as, for example, a normal saline solution, a VIPERSLIDE™ solution, a ROTA-GLIDE™ solution or a ROTABLATOR® solution or the like. The source inlet tube 14a delivers the solution through inlet port 12a and into branch 16a of the first Y-shaped tube or connector 16, which functions to connect inlet tube 14a with inlet tube 14b. Inlet tube 14b has the second fluid (such as a contrast fluid or solution or the like) and delivers the second fluid or solution or agent to be mixed the first fluid or solution or agent. Clearly, the source or inlet tubes and inlet ports may selectively connect to and provide any solutions or fluids or combinations of solutions or fluids, depending on the particular application of the mixing device, while remaining within the spirit and scope of the present invention.

Optionally, and desirably, branches 16a, 16b may have a respective control knob or dial or user input 34a, 34b (FIGS. 8 and 9) that selectively controls the percent of solution entering via inlet tube 14a and into the first Y-shaped tube 16 to be mixed with the selected percent of solution entering the first Y-shaped tube 16 via inlet tube 14b. The amount or percent of solution entering via source or inlet tubes 14a, 14b may comprise a contrast medicated solution or the like, and the contrast entering the first Y-shaped tube 16 thus can be tightly controlled to enter at the percentage rate of 0 percent (where the tube is effectively shut off or closed at the user input) to 100 percent (where the tube is fully open or unrestricted at the user input), depending on the operator's discretion and patient's renal condition. By adjusting the user inputs, the desired mix ratio can be achieved for the mixed solution, whereby, when the user draws back on the syringe plunger, the correct ratio of fluids is drawn into the syringe, and then may be readily discharged to the target container, with no contamination of the fluids in the source containers.

The mixing device 10 thus allows the total mixed solution with contrast to double, triple, or quadruple (or any other percentage or fraction) as being mixed with the other solution (such as normal saline). For example, for a given amount of fluid, such as 100 cc of saline (such as may be provided through inlet tube 14a and inlet port 12a, for example), the operator can increase or decrease the total amount of contrast used for a given quantity of mixed solution. For example, an operator may set the user input or dial or dials to allow for a 2:1 mixture (such as setting one dial to 100 percent or fully open and the other dial to 50 percent), and may then draw in the desired amount of fluid into the mixing receptacle. For example, if 150 cc of mixed fluid is desired at a 2:1 ratio, the user may set tone dial to 100 percent and the other dial to 50 percent and pull at the syringe plunger 24a (or otherwise apply a negative pressure at the mixing container) until the mixing device draws in 150 cc into the mixing container 24b, which, due to the selected settings at the user inputs and selected degree of restriction of the inlet tubes of the mixing device, would draw 100 cc of saline through one inlet port 12a and 50 cc of contrast through the other inlet port 12b. Once the desired or selected amount of mixed solution (at the desired or selected mixing ratio) is mixed in and accumulated in the mixing container 24b, the user or operator may push at the plunger 24a (or otherwise apply a positive pressure at the mixing container) to expel the mixed solution from the container 24b and through the discharge tube 28 and out through discharge port 30 and into the target container or receptacle or vessel.

Figure 8:
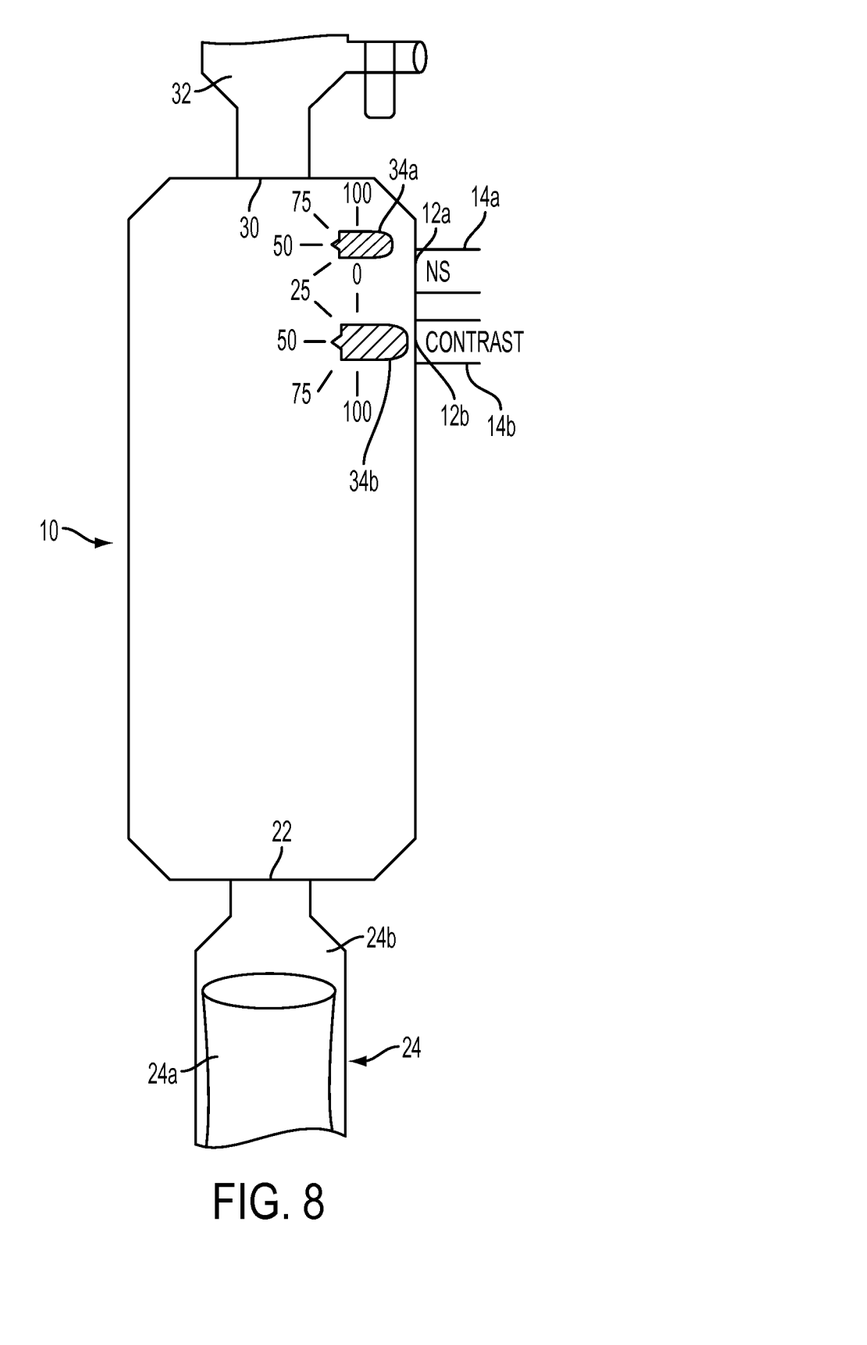
FIG. 8 is a side elevation of another fluid mixing device in accordance with the present invention.
Figure 9:
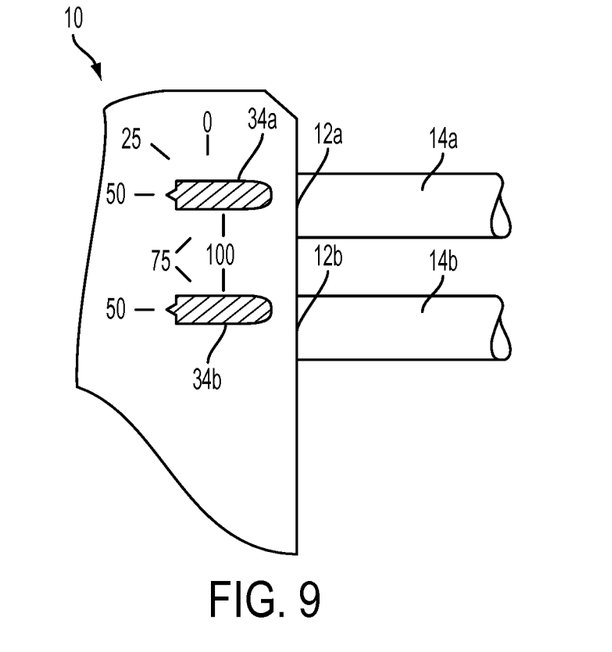
FIG. 9 is an enlarged plan view of controls suitable for use with the fluid mixing device of the present invention.

The user inputs 34a, 34b may comprise any suitable means or mechanism that selectively restricts flow through the branches 16a, 16b of the mixing device 10, such as by selectively and variably clamping or closing the tube to a selected or desired opening or passageway size. For example, and such as shown in FIGS. 8 and 9, the user inputs 34a, 34b may comprise dials that, when adjusted or rotated, impart a corresponding degree of clamping on the branches 16a, 16b in the mixing device, whereby a predetermined amount of rotation between a zero (0) indicator and a hundred (100) indicator causes a corresponding amount of clamping on the hose or tube at or near the user input, whereby the opening of the tube is at a selected size or percentage as compared to the opening in its unrestricted or unclamped state.

Figure 10:
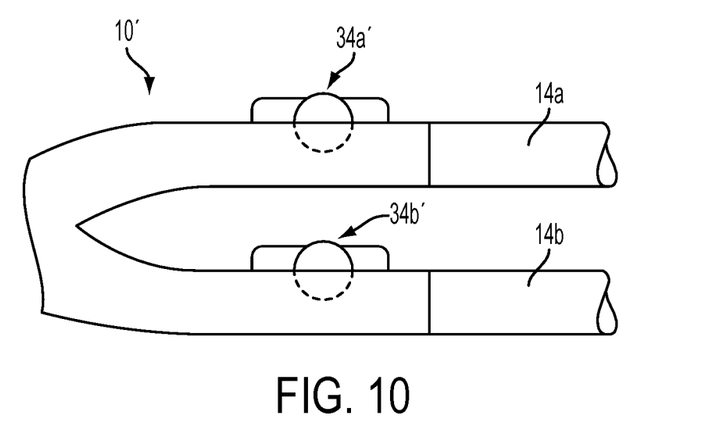
FIG. 10 is a side elevation of other flow control devices or elements suitable for use with the fluid mixing of the present invention.

Optionally, other means for controlling fluid flow through the tubes of the mixing device may be implemented, while remaining within the spirit and scope of the present invention. For example, and with reference to FIG. 10, the mixing device 10' may include user inputs 34a', 34b', which comprise clamping discs, which when, moved in one direction, move along a ramp to cause clamping or pinching of the tube a desired or selected amount, and, when moved in the opposite direction, move along the ramp to decrease the clamping or pinching of the tube the desired or selected amount. The user inputs 34a', 34b', may include a scale or gradient or indicator that indicates to the user the amount or percentage of closure of the tube for given degrees of movement of the disc along the ramp, so the operator or user can readily set the discs at an appropriate position to achieve the desired mix ratio.

As the solutions from inlet tubes 14a, 14b enter the first Y-shaped tube or connector 16, the solutions or fluids will immediately mix as they come in contact with one another, thereby forming a newly mixed saline and contrast solution or mixture that travels though the first Y-shaped tube 16 and through one way check valve 18 at the junction of tube 16c of the first Y-shaped tube 16 and branch or tube 20a of the second Y-shaped tube 20. The second Y-shaped tube 20, with its check valve 18, limits or substantially precludes the newly mixed solution from going back into the first Y-shaped tube 16 during mixing of the solutions, and, when the positive pressure is applied by the receptacle or syringe 24, the mixed fluid or solution is directed through branch or tube 20b of the second Y-shaped tube 20 and check valve 26 and out the discharge tube 28.

The negative pressure created via aspiration in the tube or receptacle 24b provides the energy needed to create motion for the solutions to move via the tubing system. Upon initiation of the negative pressure, the flow is directed immediately into the tube or receptacle 24b and is mixed together, with the one way check valve 18 allowing the fluid to flow from inlet tubes 14a, 14b into the receptacle 24b, while check valve 26 limits or substantially precludes fluid from flowing from the target receptacle 32 back through the discharge tube 28 and into the receptacle 24. Upon initiation of a positive pressure at the receptacle 24, the check valve 26 allows for fluid flow direction from receptacle 24 through the discharge tube 28 and into the target receptacle 32, while check valve 18 then limits or substantially precludes back flow of the fluid into the first Y-shaped tube 16 and back into the source containers that are in fluid communication with inlet tubes 14a, 14b. The one way check valves thus control the fluid flow dynamics and flows into and along only the desired or appropriate path or tube network for the particular function or operation of the mixing device. For example, fluid flow may only flow from inlet tubes 14a, 14b to receptacle 24, and from receptacle 24 to target receptacle 32.

The knobs or user inputs at or near the inlet ports 12a, 12b (such as on the source or inlet tubes 14a, 14b or branches 16a, 16b) control the percentage of each solution to be mixed and may provide an endless combination of solution mixtures left to the discretion of the operators and/or physicians. For example, the mixture may be a 50/50 mixture with 100 percent of each solution entering the first Y-shaped tube 16 and mixing together. An increase of one versus the other may provide any other mixture for concentration that may be selected or desired or appropriate.

Figure 11:
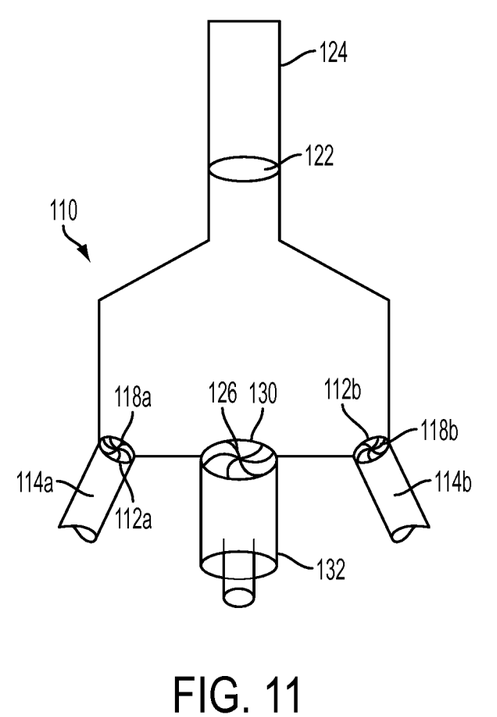
FIG. 11 is a plan view of another fluid mixing device in accordance with the present invention.

Optionally, other means for controlling fluid flow between two source containers, a mixing container and a target container may be implemented while remaining within the spirit and scope of the present invention. For example, and with reference to FIG. 11, a mixing device 110 may function in a similar manner as described above, and may include two inlet ports 112a, 112b, with one way check valves 118a, 118b at the respective ports 112a, 112b. The mixing device 110 has an inner mixing cavity and includes a mixing port 122 at an end or portion thereof, with a mixing receptacle 124 attached at mixing port 122. Mixing device 110 includes a discharge port 130, which has a one way check valve 126 disposed thereat. Thus, during use of mixing device 110, a user may apply a negative pressure at mixing container 124 to draw fluid from inlet tubes 114a, 114b into inlet ports 112a, 112b, with check valves 118a, 118b allowing for fluid flow in that direction (into the cavity of the mixing device, or optionally into and through hoses or tubes in the mixing device) and into the mixing container 124 (and while check valve 126 limits or substantially precludes drawing of any fluid from target container 132 connected to discharge port 130), such as in a similar manner as described above. After the desired or selected amount of solution is mixed and accumulated in the mixing container 124, the user may apply a positive pressure at mixing container to expel the fluid or solution from mixing container 124 back into the mixing device and through check valve 126 at discharge port 130 and into the target container 132 (and while check valves 118a, 118b limit or substantially preclude flow of any fluid from mixing container 124 and mixing device 110 to the source containers attached at inlet tubes 114a, 114b), such as in a similar manner as described above.

Therefore, the present invention provides a mixing device for mixing two fluids, such as for mixing a contrast solution with a saline solution (or other solutions or fluids as desired). The mixing device of the present invention controls the flow of the fluids into the device and into a mixing container and out of the device to a target container via one way check valves that allow for fluid flow in one direction while limiting or substantially precluding fluid flow in the opposite direction. The inlet ports or tubes may be in fluid communication with a check valve that, responsive to a negative pressure at the mixing container, allows fluid to flow from the source containers into the mixing device (where the fluids are mixed together) and into the mixing or holding container. The discharge port or tube is in fluid communication with another check valve that, responsive to a positive pressure at the mixing container, allows fluid to flow from the mixing container into the mixing device and into the target container. When fluid is drawn into the mixing device to be mixed, the discharge check valve limits or substantially precludes drawing of fluid from the target container, while, when fluid is discharged or expelled to the target container, the inlet check valve or valves limit or substantially preclude expulsion of fluid toward and to the inlet tubes and source containers. Although shown and described as mixing two fluids or solutions together to form the mixture or mixed solution, clearly the mixing device of the present invention may be modified or configured to draw in three or more different fluids or solutions and to mix the solutions and to discharge the mixture or mixed solution into a target container in a controlled manner, such as in a similar controlled manner as described above, and while remaining within the spirit and scope of the present invention.

The above descriptions are those of current embodiments of the invention. Various alterations and changes can be made without departing from the spirit and broader aspects of the present invention, which is intended to be limited only by the scope of the appended claims, which are to be interpreted in accordance with the principles of patent law including the doctrine of equivalents.

The invention claimed is:

1. A fluid mixing device for mixing fluids from at least two source containers and for discharging a mixed solution to a target container, said fluid mixing device comprising:
    first and second inlet ports in fluid communication with respective source containers;
    a first tube in fluid communication with said first inlet port;
    a second tube in fluid communication with said second inlet port, wherein said first tube and said second tube connect together into a common tube;
    at least one one-way flow inlet check valve positioned within said common tube, the at least one one-way flow inlet check valve being in fluid communication with said first and second inlet ports and said first and second tubes;
    a mixing container in fluid communication with said at least one one-way flow inlet check valve;
    a discharge port in fluid communication with a target container;
    a one-way flow discharge check valve in fluid communication with said mixing container and said discharge port; and
    a Y-shaped tube positioned between the mixing container and the discharge port, the Y-shaped tube including (i) a first branch that connects to the at least one one-way flow inlet check valve and (ii) a second branch that connects to the one-way flow discharge check valve;
    wherein, responsive to a negative pressure at said mixing container, fluid is drawn from said respective source containers through said first and second inlet ports, said first and second tubes, and said common tube, and through said at least one one-way flow inlet check valve and into said mixing container, while said one-way flow discharge check valve precludes drawing of fluid from said target container; and
    wherein, responsive to a positive pressure at said mixing container, fluid is expelled from said mixing container through said one-way flow discharge check valve and into said target container, while said at least one one-way flow inlet check valve precludes discharge of fluid from said mixing container to said first and second inlet ports and the source containers.

2. The fluid mixing device of claim 1, wherein said at least one one-way flow inlet check valve comprises a single inlet check valve disposed within said common tube.

3. The fluid mixing device of claim 2, further comprising a third inlet tube in fluid communication between said at least one one-way flow inlet check valve and said mixing container.

4. The fluid mixing device of claim 3, wherein a discharge tube is connected to and in fluid communication with said third inlet tube and extends between said third inlet tube and said discharge port, said discharge tube including said one-way flow discharge check valve.

5. The fluid mixing device of claim 1, further comprising first and second user inputs that are adjustable by a user to adjust a size of passageways of said first and second tubes to adjust an amount of fluids that flow from the source containers to the mixing container.

6. The fluid mixing device of claim 1, wherein said at least one one-way flow inlet check valve comprises first and second inlet check valves respectively disposed in fluid communication with said first inlet port and said second inlet port.

7. The fluid mixing device of claim 1, further comprising a housing, wherein said first and second inlet ports and said discharge port are disposed at an outer portion of the housing to allow for connection and disconnection of the source containers and the target container.

8. The fluid mixing device of claim 7, wherein said housing has a mixing port that allows for connection and disconnection of said mixing container.

9. The fluid mixing device of claim 7, wherein said housing includes one or more user inputs to allow a user to control a size of passageways through which fluids flow from the source containers, in order to facilitate control of a percentage of fluids in a final mixture.

10. The fluid mixing device of claim 1, further comprising first and second user inputs that are adjustable by a user to adjust passageways through which fluids flow from the source containers to the mixing container.

11. A fluid mixing device for mixing fluids from at least two source containers and for discharging a mixed solution to a target container, said fluid mixing device comprising:
a housing;
first and second inlet ports in fluid communication with respective source containers;
first and second inlet tubes in fluid communication with said first and second inlet ports, respectively, wherein said first and second inlet tubes connect together into a common tube;
at least one one-way flow inlet check valve positioned within said common tube, the at least one one-way flow inlet check valve being in fluid communication with said first and second inlet tubes;
a mixing container in fluid communication with said at least one one-way flow inlet check valve;
a discharge port in fluid communication with a target container;
a discharge tube in fluid communication with said discharge port, wherein said first and second inlet ports and said discharge port are disposed at an outer portion of the housing to allow for connection and disconnection of the source containers and the target container;
a one-way flow discharge check valve in fluid communication with said mixing container and said discharge port;
a Y-shaped tube positioned between the mixing container and the discharge tube, the Y-shaped tube including (i) a first branch that connects to the at least one one-way flow inlet check valve and (ii) a second branch that connects to the one-way flow discharge check valve;
wherein said first and second inlet tubes and said discharge tube are in fluid communication with one another;
wherein, responsive to a negative pressure at said mixing container, fluid is drawn from said respective source containers through said first and second inlet ports and along said first and second inlet tubes and through said at least one one-way flow inlet check valve and into said mixing container, while said one-way flow discharge check valve precludes drawing of fluid from said target container when the negative pressure is applied at said mixing container; and
wherein, responsive to a positive pressure at said mixing container, fluid is expelled from said mixing container through said one-way flow discharge check valve and into said discharge tube and into said target container, while said at least one one-way flow inlet check valve precludes discharge of fluid from said mixing container to said first and second inlet tubes and said first and second inlet ports and the source containers when the positive pressure is applied at said mixing container.

12. The fluid mixing device of claim 11, further comprising a third inlet tube in fluid communication between said at least one one-way flow inlet check valve and said mixing container.

13. The fluid mixing device of claim 12, wherein said discharge tube is connected to and in fluid communication with said third inlet tube and extends between said third inlet tube and said discharge port, said discharge tube including said one-way flow discharge check valve.

14. The fluid mixing device of claim 13, wherein said third inlet tube and said discharge tube comprise the first branch and the second branch of the Y-shaped tube, respectively, with a third branch of said Y-shaped tube being in fluid communication with said mixing container.

15. The fluid mixing device of claim 11, wherein said at least one one-way flow inlet check valve comprises first and second inlet check valves respectively disposed in fluid communication with said first inlet port and said second inlet port.

16. The fluid mixing device of claim 11, wherein said housing has a mixing port that allows for connection and disconnection of said mixing container.

17. The fluid mixing device of claim 16, wherein said housing includes one or more user inputs to allow a user to control a size of passageways through which fluids flow from the source containers, in order to facilitate control of a percentage of fluids in a final mixture.

18. The fluid mixing device of claim 11, wherein said at least one one-way flow inlet check valve comprises a single inlet check valve disposed downstream of a junction of said first and second inlet tubes into said common tube.

19. The fluid mixing device of claim 11, wherein said at least one one-way flow inlet check valve comprises first and second inlet check valves disposed at said first and second inlet tubes, respectively, and wherein said first and second inlet check valves are in fluid communication with a junction that joins said first and second inlet tubes into said common tube and that is in fluid communication with said discharge tube.

20. The fluid mixing device of claim 11, further comprising first and second user inputs that are adjustable by a user to adjust a size of passageways of said first and second inlet tubes to adjust an amount of fluids that flow from the source containers to the mixing container when the negative pressure is applied at said mixing container.

\* \* \* \* \*